(12) United States Patent
Bar-David et al.

(10) Patent No.: US 11,250,968 B2
(45) Date of Patent: Feb. 15, 2022

(54) CONSTRUCTIONS OF X-RAY LENSES FOR CONVERGING X-RAYS

(71) Applicant: Convergent R.N.R. Ltd., Tirat Carmel (IL)

(72) Inventors: Aharon Bar-David, Nesher (IL); Shirly Borukhin, Atlit (IL); Michael Kleckner, Ramat-Ishai (IL); Zeev Harel, Kfar-Saba (IL)

(73) Assignee: Convergent R.N.R. Ltd., Tirat Carmel (IL)

( * ) Notice: Subject to any disclaimer, the term of this patent is extended or adjusted under 35 U.S.C. 154(b) by 0 days.

(21) Appl. No.: 16/930,967

(22) Filed: Jul. 16, 2020

(65) Prior Publication Data

US 2020/0350090 A1 Nov. 5, 2020

Related U.S. Application Data

(63) Continuation-in-part of application No. 15/639,315, filed on Jun. 30, 2017, now abandoned, which is a continuation-in-part of application No. PCT/IL2015/051265, filed on Dec. 29, 2015.

(60) Provisional application No. 62/097,628, filed on Dec. 30, 2014.

(51) Int. Cl.
*G21K 1/06* (2006.01)
*A61N 5/10* (2006.01)

(52) U.S. Cl.
CPC ........... *G21K 1/067* (2013.01); *A61N 5/1042* (2013.01); *A61N 5/1084* (2013.01); *G21K 2201/062* (2013.01); *G21K 2201/064* (2013.01); *G21K 2201/067* (2013.01)

(58) Field of Classification Search
None
See application file for complete search history.

(56) References Cited

U.S. PATENT DOCUMENTS

| | | | |
|---|---|---|---|
| 2002/0004626 A1 | 1/2002 | Abe | |
| 2005/0025281 A1 | 2/2005 | Verman et al. | |
| 2005/0201517 A1 | 9/2005 | Chen | |
| 2006/0239404 A1* | 10/2006 | Udpa | A61N 5/10 378/62 |

(Continued)

FOREIGN PATENT DOCUMENTS

WO   WO2000062306 A2   10/2000

OTHER PUBLICATIONS

Nakajima et al. "Shaped Silicon-crystal wafers obtained by plastic deformation and their application to silicon-crystal lenses", nature materials, vol. 4, Jan. 2005, p. 47-50 (Year: 2005).*

(Continued)

*Primary Examiner* — David P Porta
*Assistant Examiner* — Mamadou Faye
(74) *Attorney, Agent, or Firm* — Greenberg Traurig, LLP

(57) ABSTRACT

An X-ray system for providing a converging X-rays comprises: (a) an X-ray source having an optical axis thereof; and an X-ray lens comprising at least one ring having a Bragg reflecting surface formed by a plurality of single-crystal tiles. Each tile individually comprises an adjusting arrangement enabling a tridimensional individual displacement thereof in angular and translational manner.

7 Claims, 15 Drawing Sheets

(56) References Cited

U.S. PATENT DOCUMENTS

2013/0170625 A1* 7/2013 Burshtein .............. G21K 1/046
378/148

OTHER PUBLICATIONS

International Search Report for PCT/IL2015/051265 dated Mar. 31, 2016.

* cited by examiner

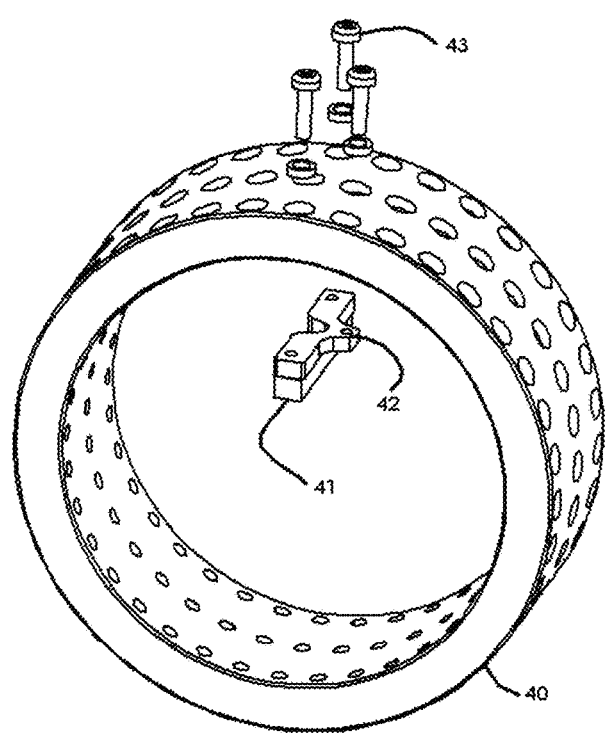
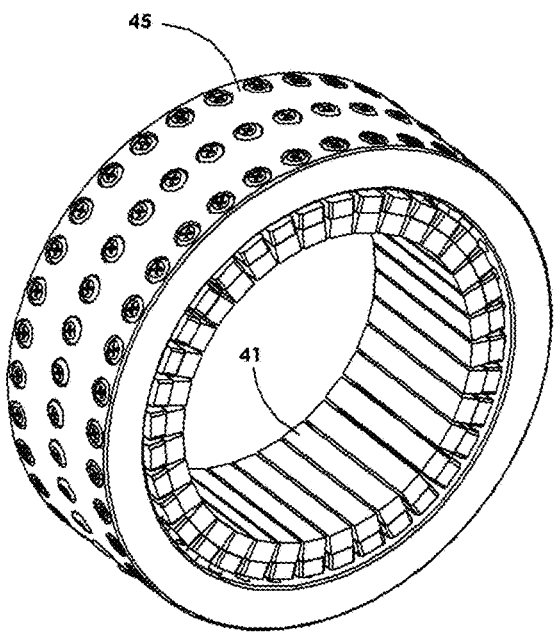
Fig. 7a  Fig. 7b
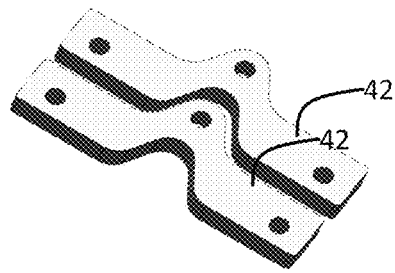
Fig. 7c

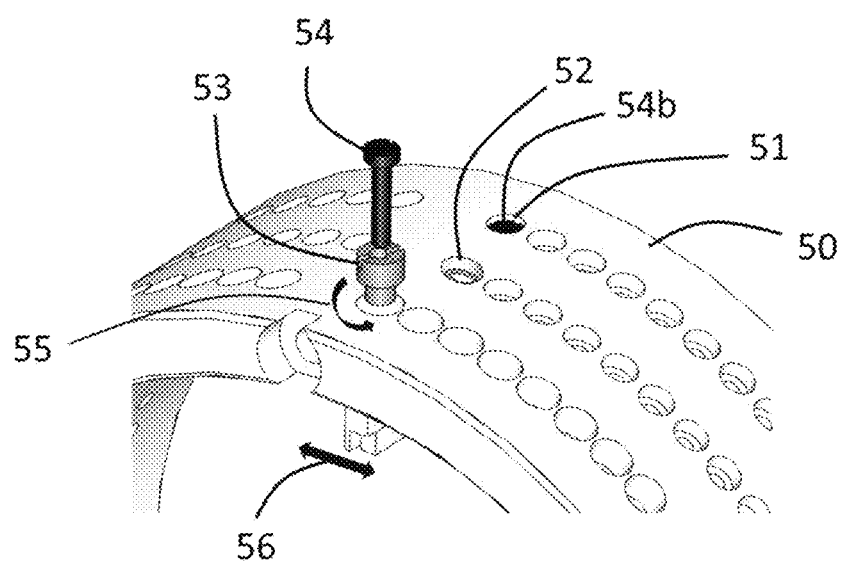
Fig. 8a
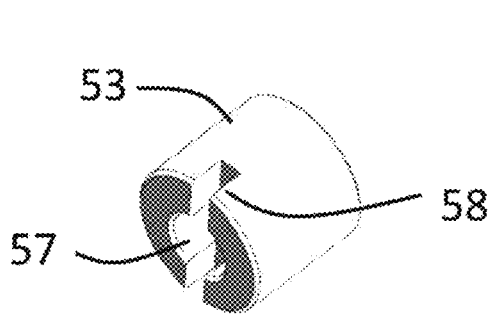 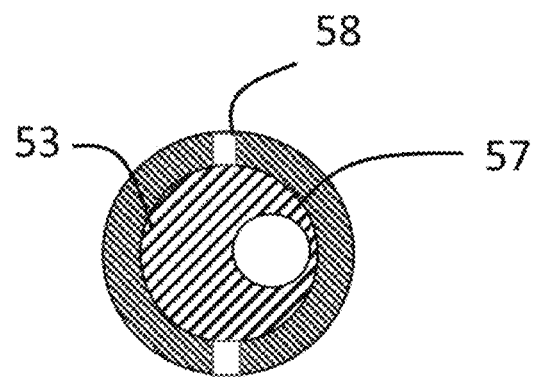
Fig. 8b          Fig. 8c

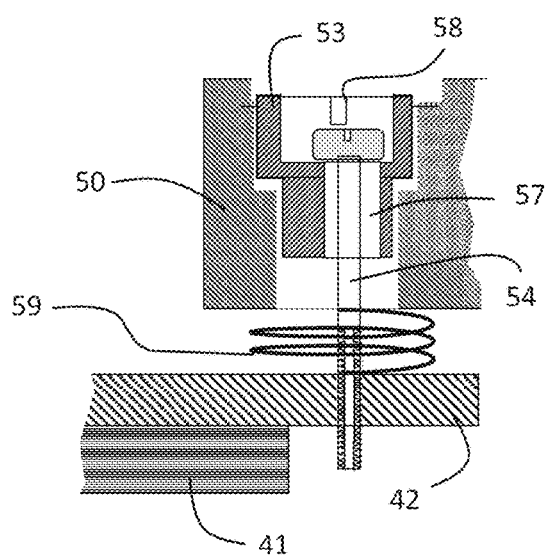 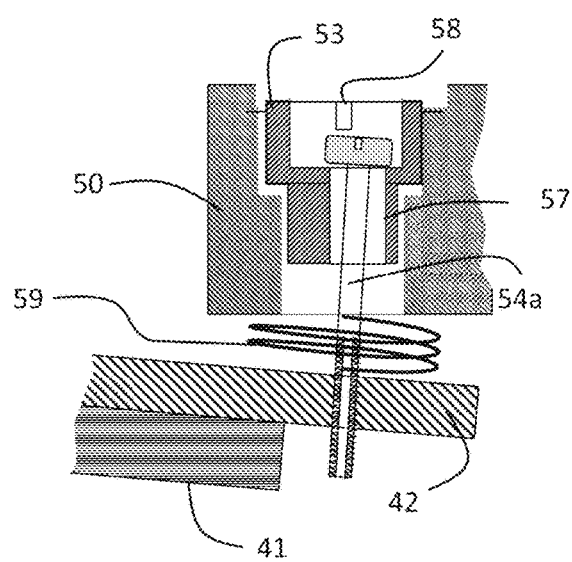
*Fig. 8d*      *Fig. 8e*

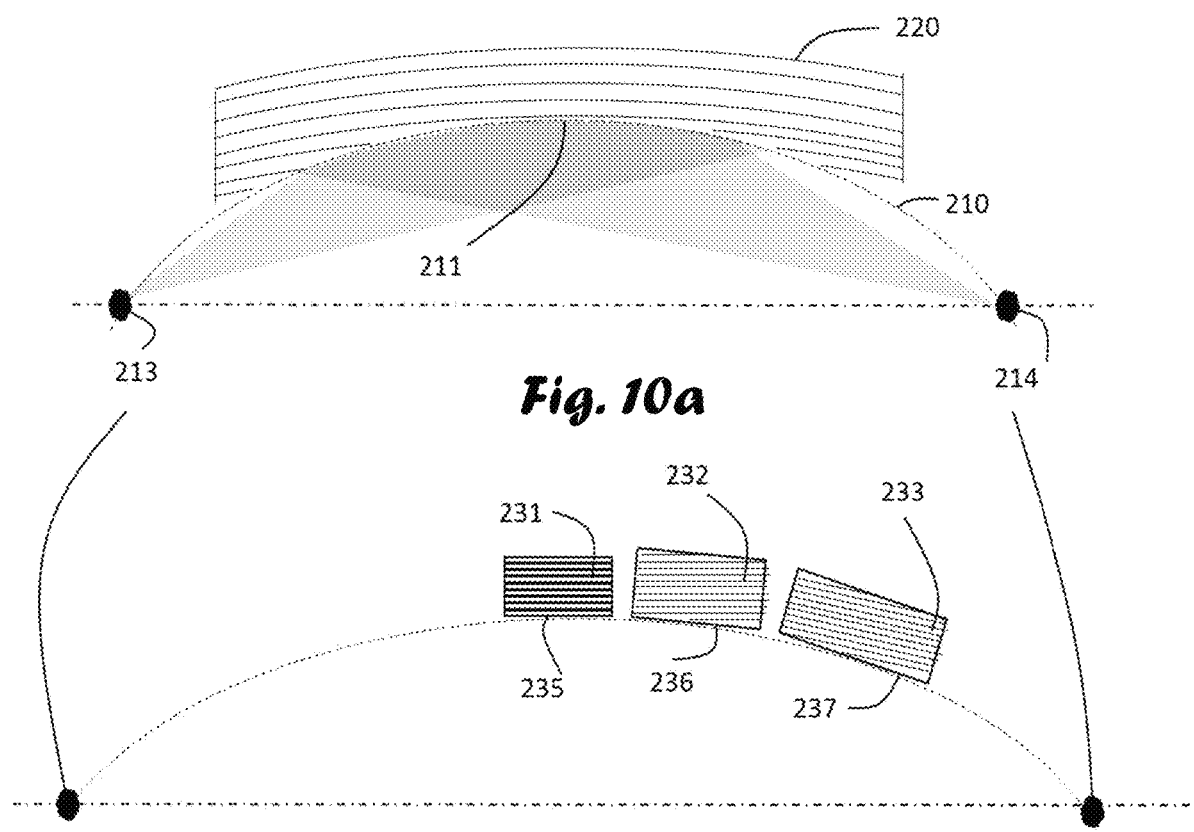

CONSTRUCTIONS OF X-RAY LENSES FOR CONVERGING X-RAYS

CROSS-REFERENCE TO RELATED APPLICATIONS

This application is a continuation-in-part application of U.S. patent application Ser. No. 15/639,315 filed on Jun. 30, 2017 claiming priority from international application PCT/IL2015/051265 filed on Dec. 29, 2015 and U.S. provisional application 62/097,628 filed on Dec. 30, 2014.

FIELD OF THE INVENTION

The present invention relates to devices for radiotherapy, radio-surgery and imaging and, more particularly, to therapeutic or imaging devices generating an adjustable convergent X-ray beam.

BACKGROUND OF THE INVENTION

Ionizing radiation equipment for the use of Radiotherapy and Radio surgery of today are mainly the Linear accelerator (LINAC), proton therapy and radioactive source devices like Gama knife. These devices are being used mainly to cure cancer. Today's existing X-ray equipment use X-ray sources that generate diverging beams. In cases where a narrow beam is needed, the techniques to narrow the beam are done by means of collimation that blocks the beam to create the desired shape. As a result only a thin portion of the beam is used with a small fraction of the generated intensity, which becomes weaker and weaker as the beam progresses. That is why to produce an effective treatment one has to rotate these instruments from many angles around the body.

Converging X-ray device had been suggested and mentioned in patent documents US2013/0170625, U.S. Pat. Nos. 6,389,100, 6,625,250, 6,606,371, 6,968,035, US 20020044626. These documents show various types of lenses for the converging of X-rays. PCT publication WO2014045273 and US2013/0170625 also shows a way to control the focal volume. Converging X-rays for medical use was mentioned in patent documents U.S. Pat. Nos. 7,070,327, 7,468,516 and US 2005/0175148.

The present invention relates to manufacturing a converging X-Rays lens that converges X-Rays to a point or to a volume, where the source can be a point source or an extended source. The construction presented here utilizes new methods and principles that have advantages in simplifying and improved methods of controlling the beam shape, size and uniformity, the beam quality, the focal region shape and size and the simplicity of manufacturing.

There are several methods known and being utilized using the Bragg law mentioned like those mentioned for example in patent documents US 2013/0170625, U.S. Pat. Nos. 6,625,250, 6,968,035 and others. The known methods are based on the Johansson and Johan principle where the reflecting units are assembled on Roland circles shape construction.

Pre-Grant publication US2013/0170625 also mentions the possibility of implementing a curved crystal surface by the use of tiles. They show tiling on a curved surface of a single ring structure containing tiny tile elements having curved surface of negative radius each.

The revealed prior art documents teach reflecting surfaces meeting Rowland circles, according to Johansson and Johann theory. However, the methods described in the present invention are different than those described in the prior art giving a more flexible and accurate control of the radiated target.

Real tumors to be treated by an X-ray radio-therapeutic device have finite dimensions of millimeters and even centimeters. The target tissues have to be irradiated in a uniform manner. Thus, there is a long-felt and unmet need for providing an X-ray therapeutic device configured for substantially uniform irradiation of the tumor.

SUMMARY OF THE INVENTION

It is hence one object of the invention to disclose an X-ray system for providing a converging X-rays comprising: (a) an X-ray source having an optical axis thereof; and (b) n X-ray lens comprising at least one ring having a Bragg reflecting surface formed by a plurality of single-crystal tiles; each tile is individually comprising an adjusting arrangement enabling a tridimensional individual displacement thereof in angular and translational manner.

Another object of the invention to disclose the single-crystal tiles processed with a non-zero offcut angle; said single-crystal tiles are spatially adjusted so that a Johansson curved surface is approximated.

A further object of the invention to disclose the single-crystal tiles processed with zero offcut angle; said single-crystal tiles are spatially adjusted so that a quasi-focusing Johann curvature is approximated.

A further object of the invention to disclose at least one single crystal tile mounted on a holder adjustably secured to said at least one ring by means of three screws.

A further object of the invention to disclose at least one of said three screws which is spring-controlled.

A further object of the invention to disclose at least one of said three screws mounted within an eccentrically arranged bore of bushing such that rotation of said bushing provides transversal displacement of said holder secured by said at least one of said three screws.

A further object of the invention to disclose the screw mounted within a diameter of said eccentrically arranged bore is sufficient for free movement therethrough in a skewed position.

BRIEF DESCRIPTION OF THE DRAWINGS

In order to understand the invention and to see how it may be implemented in practice, a plurality of embodiments is adapted to now be described, by way of non-limiting example only, with reference to the accompanying drawings, in which

FIGS. 7a to 7e show a 3D drawing of an adjusting system for individual tiles

FIGS. 8a to 8e show an eccentric bushing arrangement

FIG. 10a shows a theoretical reflecting surface of exact theoretical principle;

FIG. 10b shows an exemplary implementation of the present invention.

DETAILED DESCRIPTION OF THE PREFERRED EMBODIMENTS

The following description is provided, alongside all chapters of the present invention, so as to enable any person skilled in the art to make use of the said invention, and sets forth the best modes contemplated by the inventor of carrying out this invention. Various modifications, however, are adapted to remain apparent to those skilled in the art, since the generic principles of the present invention have been defined specifically to provide a control to the volume and shape of an X-ray system arranged for converging X-rays to a focal region.

The term "symmetric structure" refers to a ring whose rotational center is on the optical axis and whose longitudinal midpoint is half way from the source to the focal region.

The term "longitudinal midpoint" refers to the longitudinal middle point of a tile and/or a ring.

The term "off-cut angle" refers to the angle between the crystal reflecting surface (31) and the desired crystallographic plane (32)—see S in FIG. 4.

The term "concentric" refers to rings that are nested one within another and having a common center.

The term "coaxial" refers to rings that share a common axis spaced one from the others along the common axis.

Figure 4A:
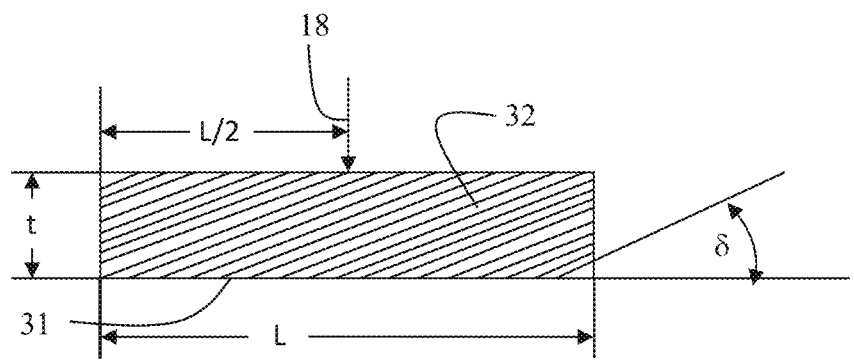
FIG. 4a shows a schematic diagram of the cross-section of a general single crystal tile with the internal structure and orientation of the desired crystallographic planes relative to the tile reflecting surface, making an angle between the crystallographic planes and the reflecting surface of the tile.
Figure 4B:
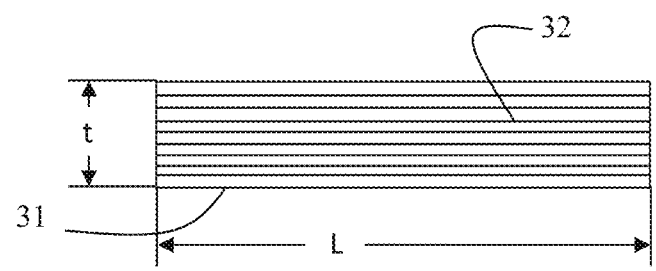
FIG. 4b shows a schematic diagram of the special case of the cross-section of a single crystal tile with desired crystallographic planes parallel to the tile reflecting surface.
Figure 4C:
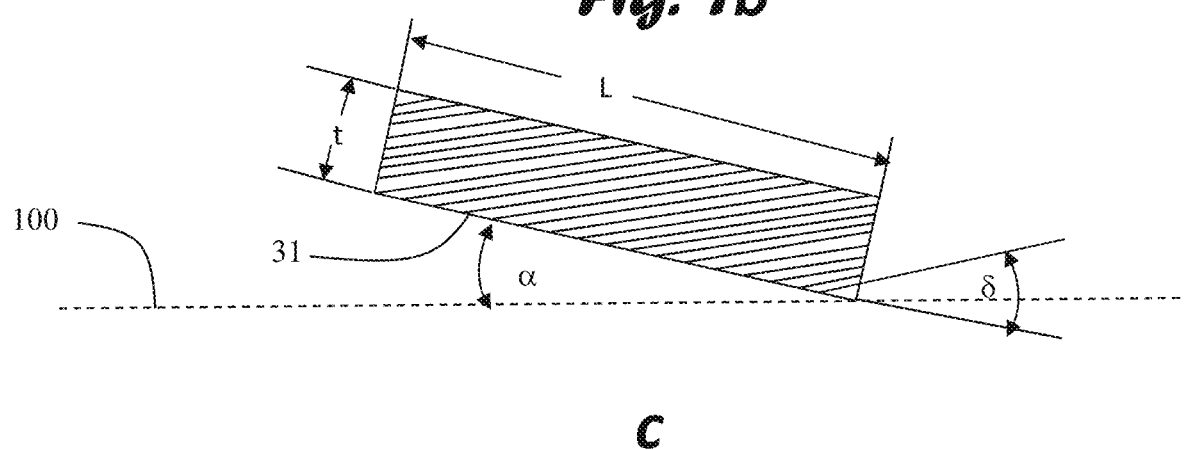
FIG. 4c shows a schematic diagram demonstrating a tilt angle of a tile forming rings of which a longitudinal cross-section reflecting surface forms a tilted angle relative to the optical axis, and the crystallographic planes form an angle different from the first mentioned, relative to the optical axis and/or the reflecting surface.

The term "tilt angle" refers to the angle between the reflecting surface (31) and the optical axis (100)—see α in FIG. 4c.

The term "extensions" refer to individual rings that are part of an extended coaxial structure.

The Johann and Johannsson theory describes a Rowland surface which is also curved longitudinally. This invention describes the approximation of the Rowland surface in a way different from the other methods allowing also the utilization of controlling a volume by the deviation from the Rowland curvature. The method has mainly to do with the longitudinal tiling of the Rowland surface (unlike the transverse tiling mentioned in other patents) and utilizes the fact that Rowland radius is very large. Thus, the coaxial rings, which implements the longitudinal tiling use the tiles with the same Miller indices as the adjacent ring (unlike different Miller indices which are used in in a concentric ring structure described in other patents). An approximation using planar tiling by the coaxial longitudinal placing of additional rings requires a very small change in angular orientation of the tiles to approximate bending of the surface with the same Miller indices. This is done by adjusting the individually each tile separately, allowing the overall structure of the ring that holds the tile to be identical to adjacent ring and only for very small changes in radius might be needed in far coaxial located rings (if any) and the curvature change is done mainly by the individual tile orientation adjustment using an invented mechanism described ahead.

A basic structure of a lens consists of a set of concentric rings comprising crystal tiles of various different crystallographic planes. An extension relates to another ring in a sense of extending it and adjusting its tiles accordingly. Extending a specific ring originally is done with the use of a reflecting material that is similar to the original ring with a slight change and mounting it coaxially on the same axis further away appending the previous ring. This slight change in location and orientation of the reflecting material is due to a slight difference in the Bragg angle because of the different location along the optical axis close to the Rowland surface. Usually it is the same material with the same crystallographic plane (Miller index) having its reflecting surface cut with a different off-cut angle and mounted at a different tilt, thus, forming the extension ring to have a conical shape.

The term "extended structure" refer to a basic structure (concentric) where at least one of the rings has at least one extension assembled in a coaxial structure appending it as explained above (mainly as in FIG. 2a) to provide a form of longitudinal tiling of rings.

This invention also allows a deliberate calculated deviation from the exact theory i.e. form the Rowland circle and from the exact off-cut angle and exact tilt angle in order to control the radiated volume and shape.

Figure 1:
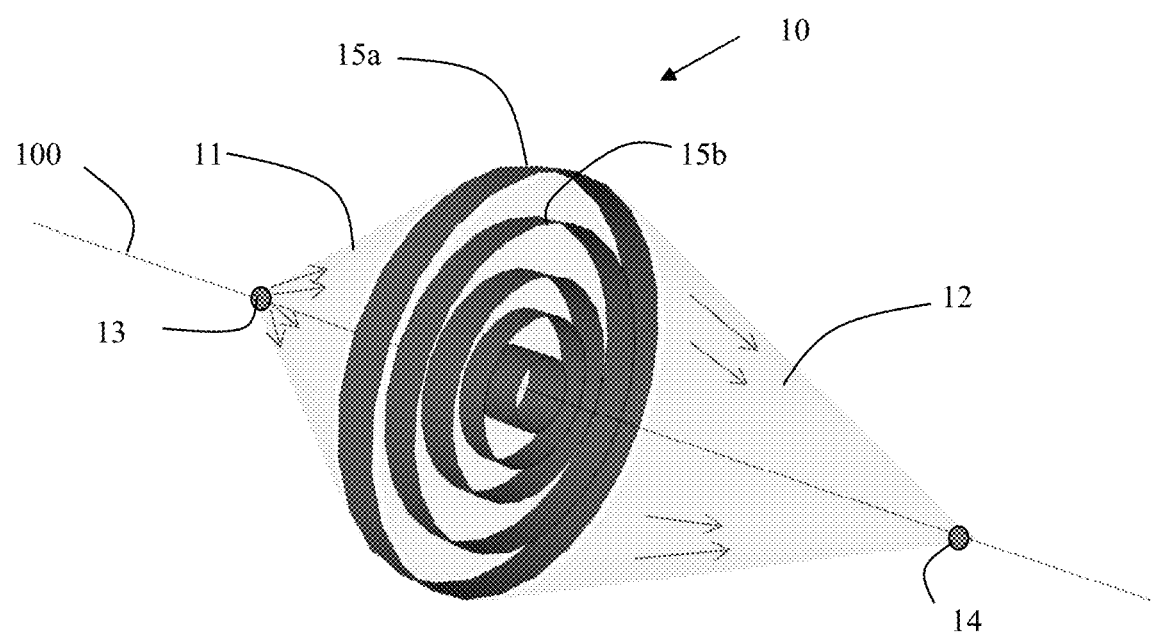
FIG. 1 is a 3-dimensional schematic diagram of an X-ray lens with an example of concentric rings construction.

Reference is now made to FIG. 1, schematically illustrating a lens system with an example of a structure of concentric rings. An X-ray source (13) emits diverging X-rays (11) that enters the lens (10) made of concentric rings (Numbered examples are the outer rings 15a and 15b). The rings reflect X-Rays in a converging manner (12) to a focal location (14).

Figures 2A, 2B:
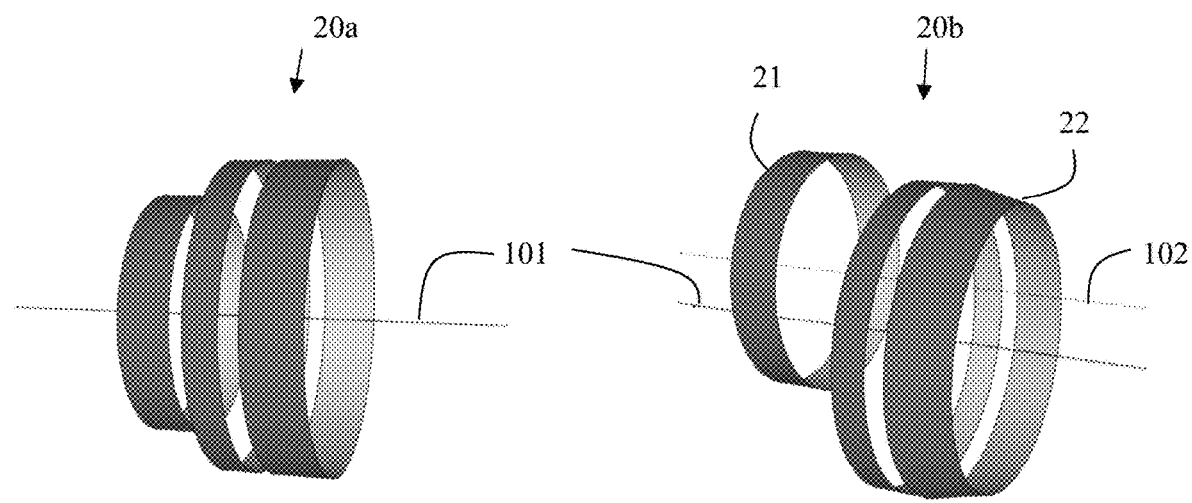
FIG. 2a is a 3-dimensional schematic diagram showing several rings arranged in a non-concentric coaxial structure.
FIG. 2b is a 3-dimensional schematic diagram showing several rings in a non-concentric and non-coaxial structure.

Reference is now made to FIGS. 2a and 2b. The lens includes several rings. FIG. 2a shows several rings assembled in a coaxial structure (20a) relative to their rotational axis (101). FIG. 2b shows example of a structure of rings (20b) assembled in a non-coaxial and non-concentric structure. Ring 21 is located in a non-coaxial manner whose rotational axis (102) does not coincide with the rotational axis of the other rings (101). Ring (22) is an example of a ring whose reflecting surface longitudinal profile is tilted relative to its rotational axis (101). In this example the ring (22) surface forms a conical structure. All rotational axes might be parallel and/or coincide or not parallel and/or not coincide to the optical axis (100).

Figure 3:
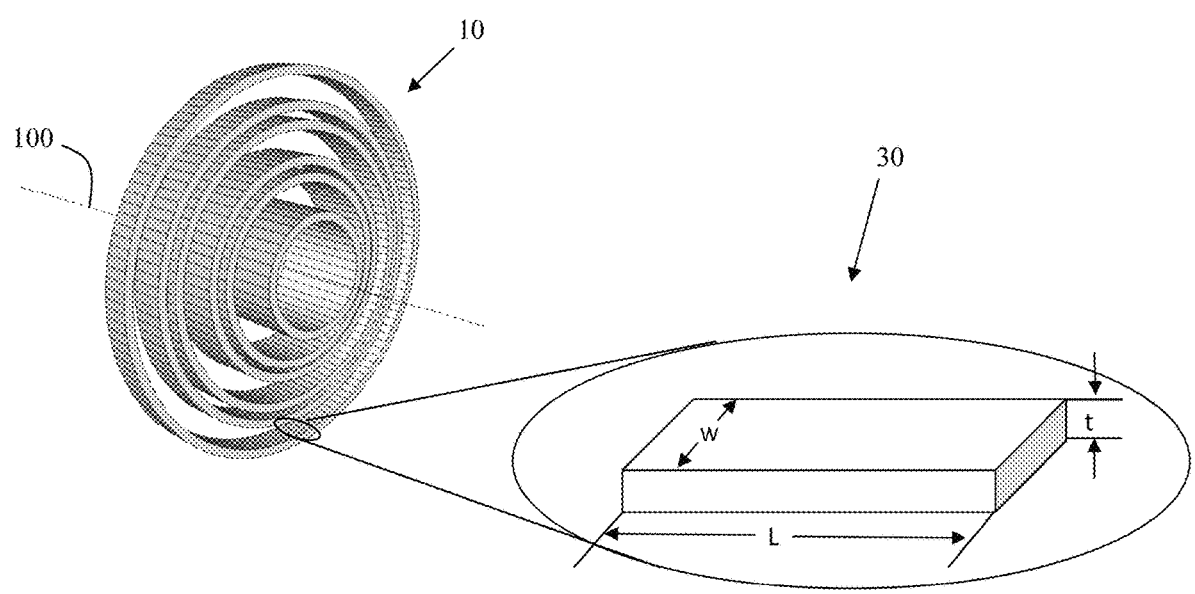
FIG. 3 shows a 3-dimensional schematic structure of rings constructed from small single crystal tiles with a magnified description of a single tile.

Reference is now made to FIG. 3, schematically illustrating a lens system (10) whose rings are made of tiles. A magnified illustration of a tile (30) is shown as well. L is the general longitudinal dimension that might be parallel to the optical axis (100), t is the tile thickness and w is the tile width whose direction is generally transversal to the optical axis (100).

Reference is now made to FIGS. 4a to 4c. FIG. 4a schematically illustrates a longitudinal cross section along the L direction of a single tile. Generally, the direction of the cross section of the desired crystallographic planes (32) forms an angle δ with the reflecting surface of the tile (31). The longitudinal midpoint (18) of a tile is located at the longitudinal middle (L/2) of the tile. FIG. 4b illustrates the special case where the desired crystallographic planes are parallel to the reflecting surface of the tile (δ=0). FIG. 4c shows a tilted tile that forms a tilted longitudinal ring profile similar to shown in FIG. 2b (Ring 22). The tilt angle is a in the figure relative to the optical axis (100).

Figure 5A:
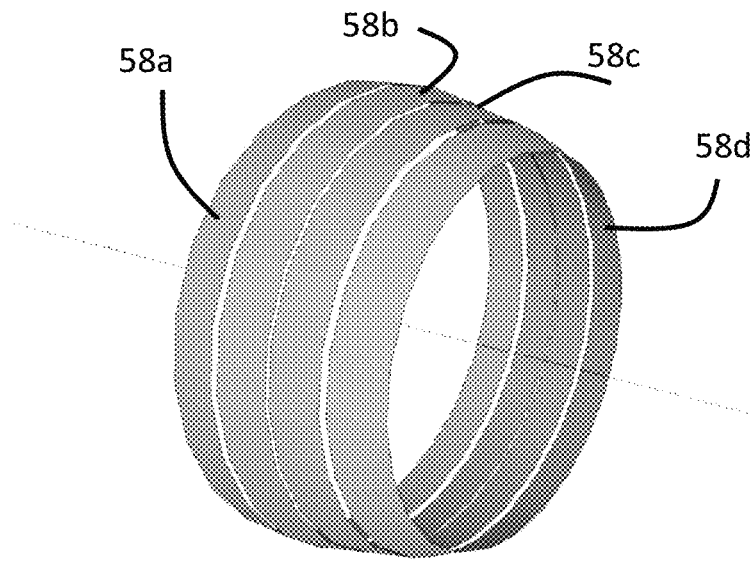
FIGS. 5a and 5b shows a 3D presentation of the extended structures.

Reference is now made to FIG. 5a schematically illustrating a diagram of a 3 dimesional structure of a single ring with its extensions. The first ring 58a acting as the first extension with the following extensions 58b, 58c and 58d. They are all the extensions that can be made, for example, from the same crystallographic planes (same Miller index) having different radii, different tilt angle and different off-cut angle. The starting point of the design is around the Rowland circle with the matched crystallographic plane adjusting the tilt and off-cut around according to the Johann and Johansson theory. Further consideration is that in this design one can deviate from the Rowland radius, tilt and off-cut angle to aim to a treated volume with a controlled shape and size. These means are an additional different means described in other projects of converging beams.

Figure 5B:
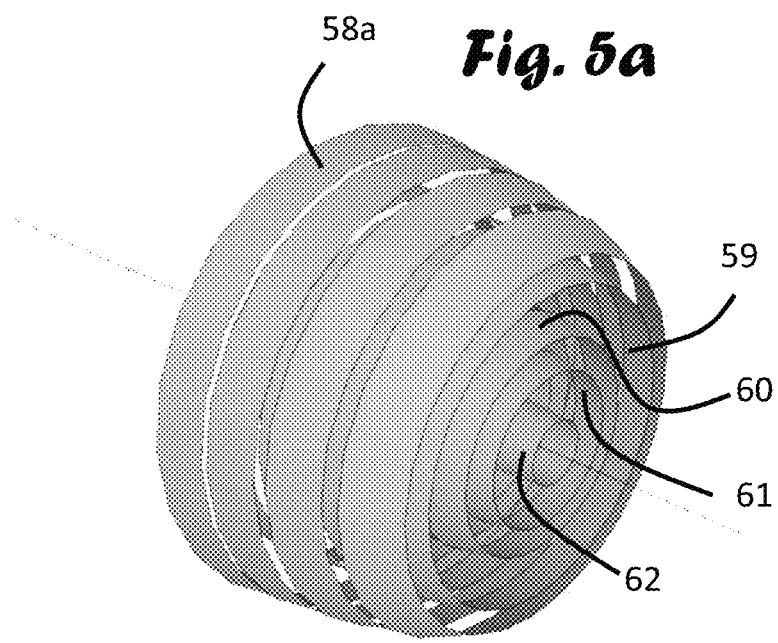

Reference is now made to FIG. 5b schematically illustrating a diagram of a 3 dimesional structure having additional multi ring construction where the structures 59, 60 61 and 62 form a concentric structure of multi rings, each having its own extensions.

The purpose of this structure is to aim the reflection from each extension to the neighborhood of the volume of interest. The deviation from Rowland radius, tilt and off-cut determines the size and shape of the neighborhood, thus, influence the size and shape of the irradiated volume.

Figure 6A:
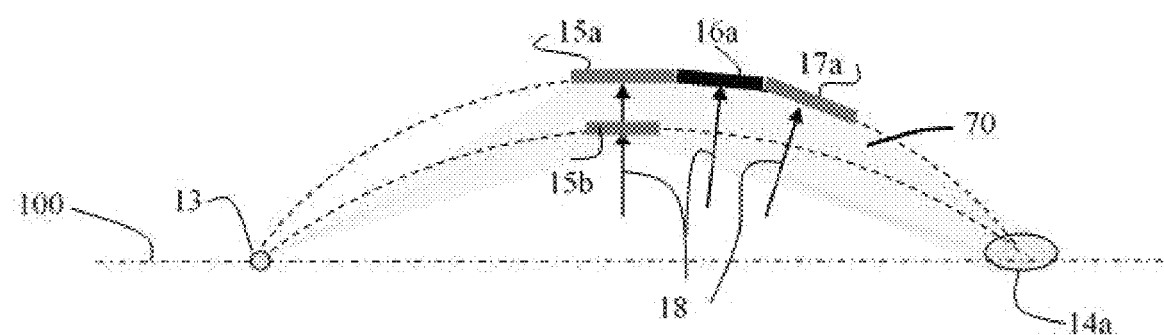
FIGS. 6a and 6b shows a schematic diagram of a two-dimensional longitudinal cut of tiles from 4 rings, where 3 rings are assembled in an extended structure.

Reference is now made to FIG. 6a schematically illustrating a diagram of a two-dimensional longitudinal cut of tiles of an example having 4 rings located on an approximate structure of Rowland circles. Tiles 15a and 15b are concentric in a symmetric structure with longitudinal midpoint (18) half way between the source (13) and the focal region (14a). Tiles 15a, 16a and 17a are coaxial in this example and form a set of extensions. This configuration is an example of a lens configured to form the smallest focal region possible with the particular tiles. The outgoing reflected beam (70) from all rings is compacted together at the focal region (14a). This is according to the Johansson and Johann theory. Only the sizes of the tile are the main cause of the broadening of the target volume. In order to have the smallest focal region possible the rings have to be assembled to form structures where the longitudinal midpoints are located on the appropriate Roland circles. Additionally, the tiles reflecting surface are tiled in an angle α so as to be tangent to the Roland circle at their longitudinal midpoint and their off-cut angle δ is obtained by grinding the single crystal tiles according to the Johansson or Johann theory calculated at the longitudinal midpoints (18) locations of the tiles on the Roland circle. The midpoints (18) of tiles 16a and 17a in this example are located at a different distance to the source (13) than the distance to the targeted location (14a), in this example closer to the target (14a). However, it is possible to locate them closer to the source (13).

Figure 6B:
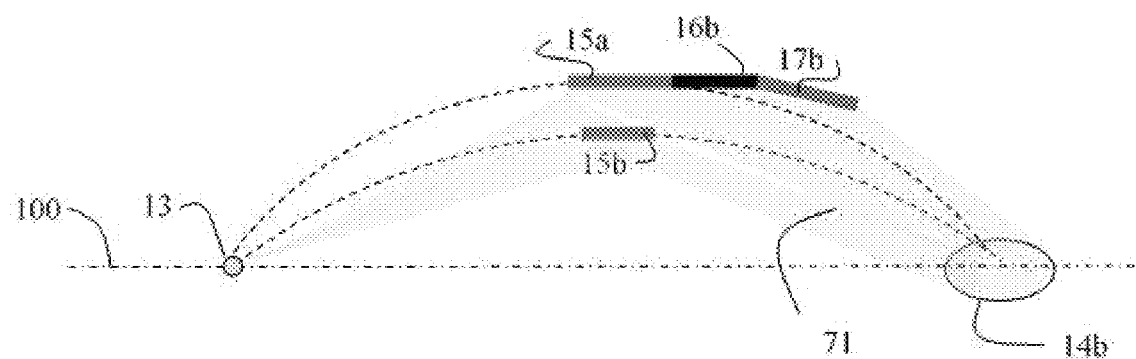

Reference is now made to FIG. 6b schematically illustrating a diagram of a longitudinal cut of tiles of an example having 4 rings made of tiles, where the structure of tiles is deviated from the Roland circles structures and the Johansson and Johann theory. Tiles may possess only an off-cut angle and not be tilted. As an example, for this, in FIG. 6b, the ring 16b is drawn parallel to the optical axis (100) as an extension to ring 15a (originally parallel), and the only difference between them is the off-cut angle δ which is 0 in 15a and different from 0 in 16b. Tiles may be only tilted with no off-cut angle. Longitudinal midpoints of the tiles may be located at different radii than those related to the Roland circles. The deviation of the extended structure spreads the reflected beam (71) so the volume of the radiated targets (14b) becomes larger.

Any combination of radii, tilt angles, off-cut angles may be employed according to the consideration described below.

The location of the tiles, their dimensions (length, width and thickness) their tilt and/or off-cut angles are designed to control the following:
1) The size and shape of the focal region.
2) Avoiding radiation blocking amongst the rings.
3) Beam radiation cross-section fill-up.
4) Uniformity considerations and
5) Simplicity of manufacturing.

Thus may deviate from the Roland circle structure and the Johansson and Johan theory. Tile sizes play a role in the design as well—they also controls the energy spectral width and values on the spectrum emitted by the source, for example at the neighborhood of the Kα location of a tungsten spectrum one may control the spectral width to determine whether to include Kα1 and Kα2 or even Kβ characteristic radiation or not, thus controlling beam quality.

Reference is now made to FIG. 7a schematically illustrating the adjustment system of individual tiles (41). The tile (41) is to be glued on a small metal holder (42) that has 3 screw threads. Combination of small turnings of the 3 screws enables individual angular adjustment of each tile (41) such that the X-ray source (not shown) is seen by the crystallographic planes of the tiles which reflect the X-ray radiation towards the desired location. This adjustment enables the correction of crystallographic plane alignment even if the actual value of the offcut is not accurate. The holder (42) is mounted to the ring (40) via holes through the ring body. Small springs hold them in place.

Reference is now made to FIG. 7b schematically illustrating a complete ring (40) fully populated with tiles. The screws heads are seen on the outer surface of the ring. They allow the adjustment of each tile individually.

Reference is now made to FIG. 7c schematically illustrating a magnified picture of a pair of tile holders (42). Combination of 3 screws enable two-axis adjustment. The middle thread is off the line interconnecting the 2 end threads near at the terminals of the holder. By turning the 2 terminal screws the tile is displaceable in the pitch direction. The middle screw displaces the tile in the roll direction. Turning all screws in a synchronic manner radially displaces the tile in order to adjust the radial distance to the ring center. Applying a combination of more than one screw adds up additional movements for example making the tile face somewhat skewed sideways making reflection correction to target the desired location. Even though the middle screw is outside the line connecting both end screws, still it is possible to mount the holders adjacent to each other. To illustrate this possibility 2 adjacent holders (42) are shown mounted next to each other in FIG. 7c.

Figure 7D:
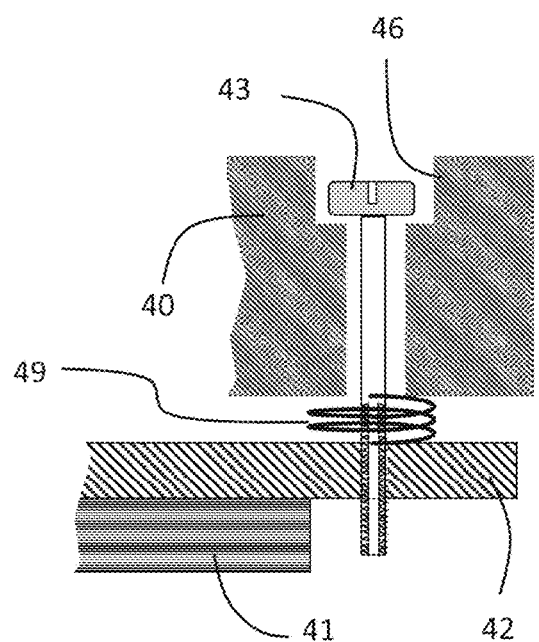
Figure 7E:
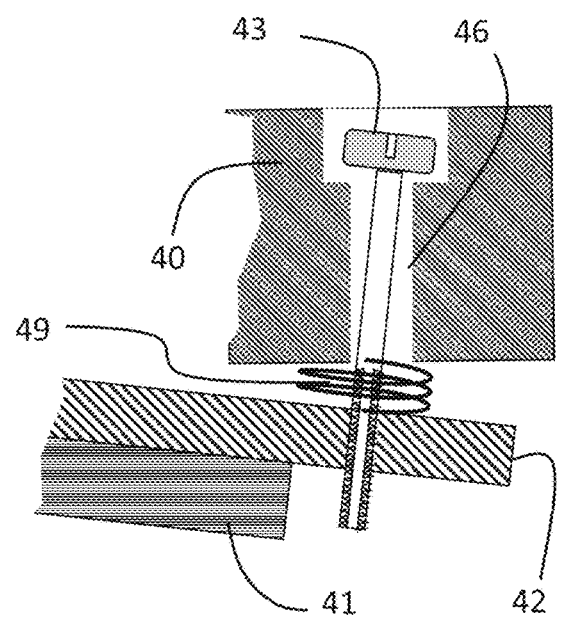

FIG. 7d shows an example how to make the connection between the end of the tile holder (42) with the glued crystal on it (41) to the ring (40). The screw goes through a hole with a counterbore (46), slightly larger than the screw, where the screw is inserted into and is screwed to the threaded hole in the tile holder tightened through a spring (49) to be held in place and at the same time also to be able to have small corrections that requires small movements that might involve skewing of the holder as seen in FIG. 7e. The tile (41) and holder (42) are skewed with the skewed screw (43) and pressed against the spring (49) and is skewed relative to the ring (40). This is possible due the larger size of the hole with counterbore (46).

FIGS. 8a to 8e show an exemplary embodiment enabling rotational corrections around the yaw axis.

In FIG. 8a moving screw (54) is inserted into an eccentric bushing (53) (shown separately in FIGS. 8b and 8c), the hole (57) for the screw (54) is drilled off-center of the bushing. The bushing body (53) is inserted to a hole with larger counterbore accurately drilled. The screw hole (57) for the passage of the screw is larger than the screw diameter to allow free movement of the screw even in, in a skewed position of the screw (54) within the bushing (53). Two notches (58) are made on the bushing body (53) so that the bushing (53) can be turned (55) separately so that screw is displaceable in the translational direction. FIGS. 8d and 8e show that the screw hole with counterbore (57) is large enough so that the screw is freely movable in the skewed position as in FIG. 8e. As shown in FIG. 8a, one terminal hole is made similar to the holes in FIG. 7a with the screw marked (54a) and the other side edge is using a bushing with screw (54), thus the translational movement may make a small difference in the distance between them. Thus, each tile is displaceable in the yaw direction. The spring (59) tightens the assembly in place while allowing all these movements. The middle hole (52) is also a bit larger than the screw diameter to allow small displacements with these adjustments.

Figure 9:
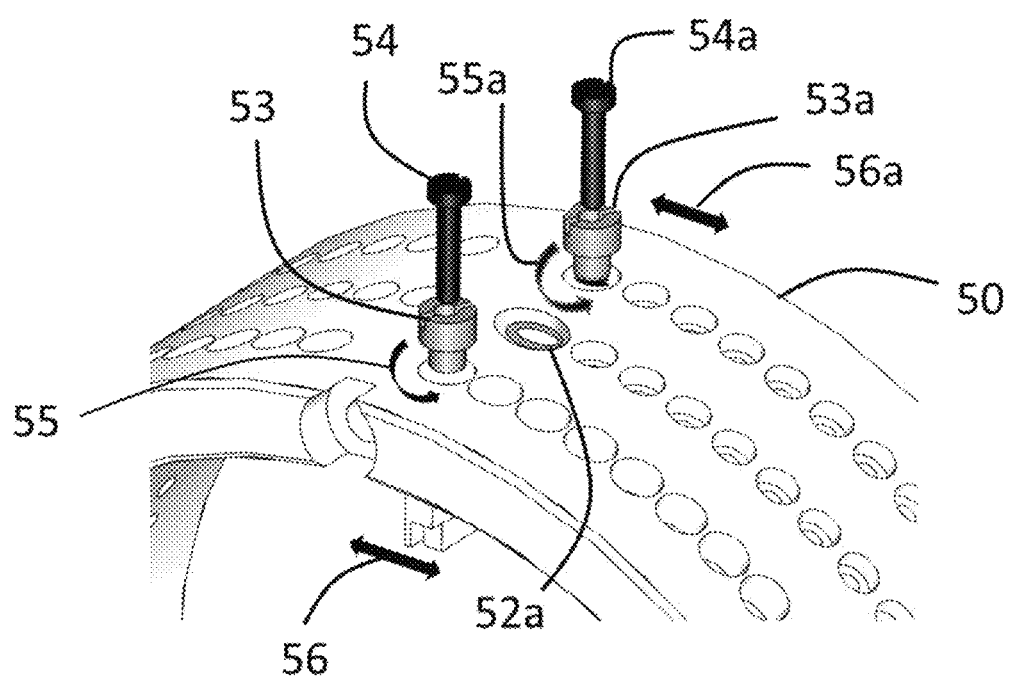
FIG. 9 shows an eccentric bushing arrangement providing a translational displacement.

FIG. 9 shows an alternative embodiment having two bushings (53 and 53a) with screws (54 and 54a). This embodiment enables a larger yaw range and the ability to make individual translational movements indicated by numerals (56 and 56a) of the tiles by synchronically turning (55 and 55a) the bushings (53 and 53a). This includes the enlargements of the middle hole (52a) accordingly.

Reference is now made to FIGS. 10a and 10b schematically illustrating the theoretical basis on which the invention allows the adjustments and also to deviate from.

FIG. 10a shows a theoretical ray tracing diagram relating to Johannsson surface. The source 213 is a small dimension type (near a point source in theory) and the target 214 will be manifested as a small theoretical volume. The reflecting surface 211 is a curved surface with the shape having Rowland radius. The crystal which is a large bent crystal has its crystallographic planes bent to twice the Rowland radius (R)–2R. Thus, the crystal planes are bent to 2R and the reflecting surface is therefore grinded to a form a surface of one R radius.

The structure described above can be approximated by implementing of planar tiles arranged into:
1) A tiled ring having planar tiles circumferentially distributed over the ring;
2) A plurality of extension rings (see FIG. 10b). Longitudinally tiling of a surface.
3) The means of deviating from the theoretical surface as a mean of controlling the treated volume shape.

FIG. 10b shows the implementation of a structure maximally close to the theory. In FIG. 10b presents the embodiment of the present invention including longitudinal tiling implemented with 3 extension rings. The shown longitudinal cross-section of tiles belongs to extension rings.

Since the reflecting surface has a curvature of R and the crystallographic planes have a curvature of 2R each longitudinal ring must employ crystals with different off-cut angle. Their reflecting surface must be tangent to R and the crystallographic planes must be tangent to 2R. Thus, in the example of FIG. 10b the tile with crystallographic plane 231 has zero offcut angle with its reflecting surface 235. The planes 232 have a non-zero offcut angle with their reflecting surface 236 and the planes 233 have a different offcut angle with the reflecting surface 237. Additionally, their tilt angles are also different. Thus, the rings closer to the target have a conical shape with larger cone angle. This implementation is a Johannsson approximation which is the closest to the theory as possible with the use of tiled rings extensions.

However, the intention of this invention is also to radiate larger volumes, make construction easier and simpler and to control the shape of the volume with the use of new techniques.

Figures 11A, 11B:
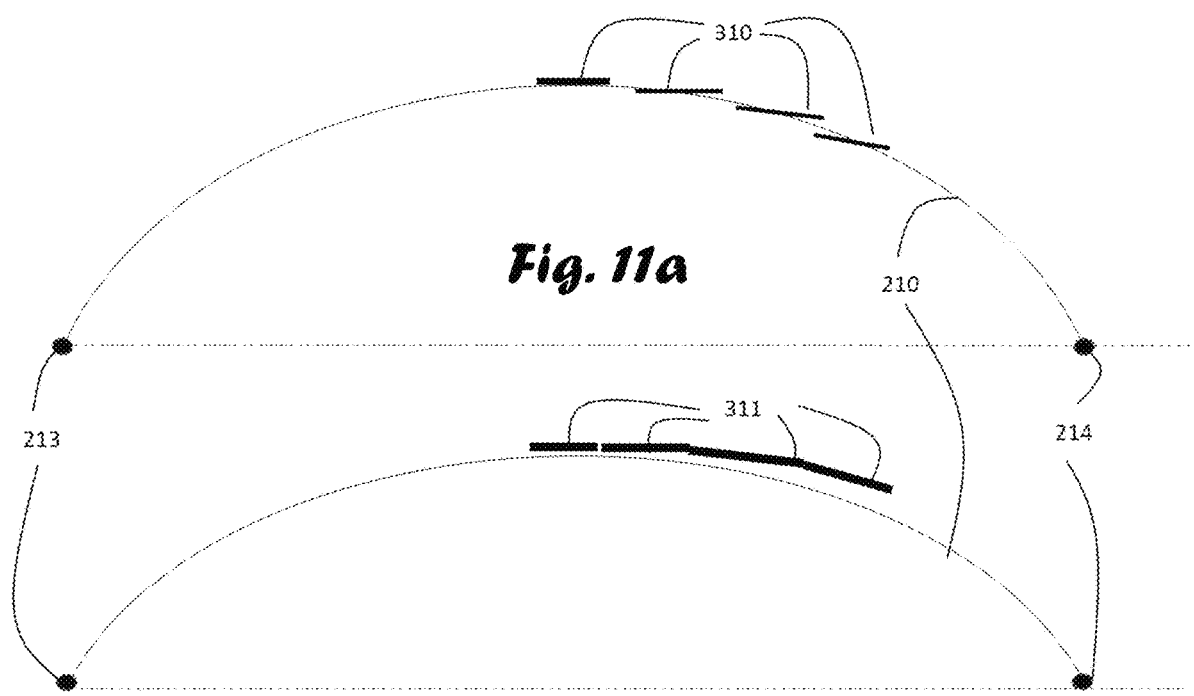
FIG. 11a shows an example of longitudinal tiling approximation arrangement.
FIG. 11b shows an additional exemplary optical arrangement of the present invention.

One possible technique is to avoid different offcut angles when manufacturing the tiles. A simple choice is to choose off-cut 0. Using such tiles with a zero-offcut angle is the approximation of Johann and is somewhat less accurate—a quasi-focusing technique. Examples of other implementations of tiling are shown in FIGS. 11a and 11b. In this case one uses all the tiles as 0 off-cut angles in the approximations.

FIG. 11a show the implementation of a Johannsson tiling but using all zero off-cut tiles. The center of the tiles is located on the Rowland surface with their tilt angle is such that it is tangent to a 2R radius, thus, giving the surface a flaked surface shape.

Another way to manifest the surface is shown in FIG. 11b showing an example of the possibility of deviating from the theory. One might like to capture all the radiation in a certain solid angle. The idea is to disregard the Rowland circle (210) but not to go too far from it. The idea is to take 0 off-cut angle tiles and to arrange them so that the extensions touch each other back to front (311) closing all spaces not allowing any ray to sneak out. The position is now determined not on the Rowland envelope but from placing the tiles front to back as connecting the adjacent rings to each other. According to this position the tilt is adjusted to the Bragg angle as seen in the new position. Thus, the reflection deviates from the target direction to enlarge and change the target size and shape. The tilt of the tiles i.e. the cone angle of the extension ring is now different from the theory. The price for this is that the focusing is not exact. Thus, the radiated volume is larger. In some cases, this is acceptable and even desired. This is an approximation more towards a Johann surface (rather than Johannsson surface).

Another deviation from the Rowland envelope is possible by direct calculation of the change in the direction of the reflected beam according to the desired deviation from the focal point to enlarge the focal size and shape. This can be done for example by changing the location and angle of the added ring center axis relative to the optical axis.

Figure 12:
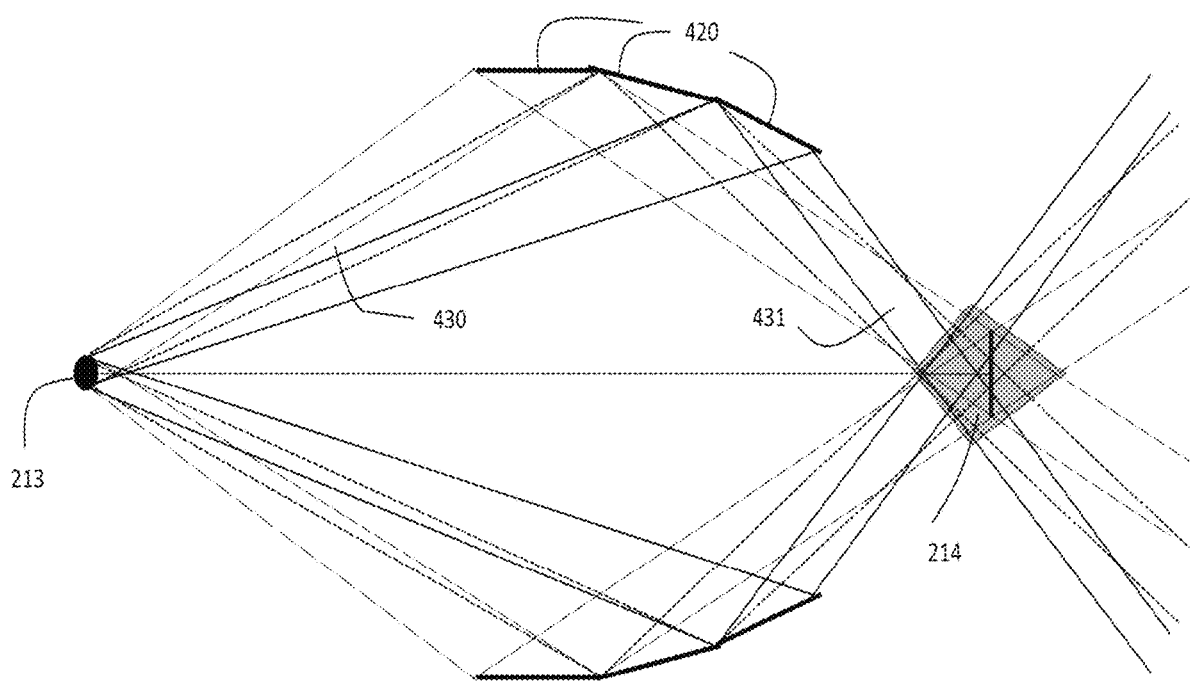
FIGS. 12 and 13 show ray tracing diagrams of exemplary optical arrangements.

Reference is now made to FIG. 12. Showing the results of the previous examples back to front connection The tiles are located somewhat away from the Rowland location thus the incoming rays (430) that collect the rays from the source (213) at Bragg angle are reflected (431) in the neighborhood of the theoretical focal region (214) making 214 larger (as marked in the figure).

Figure 13:
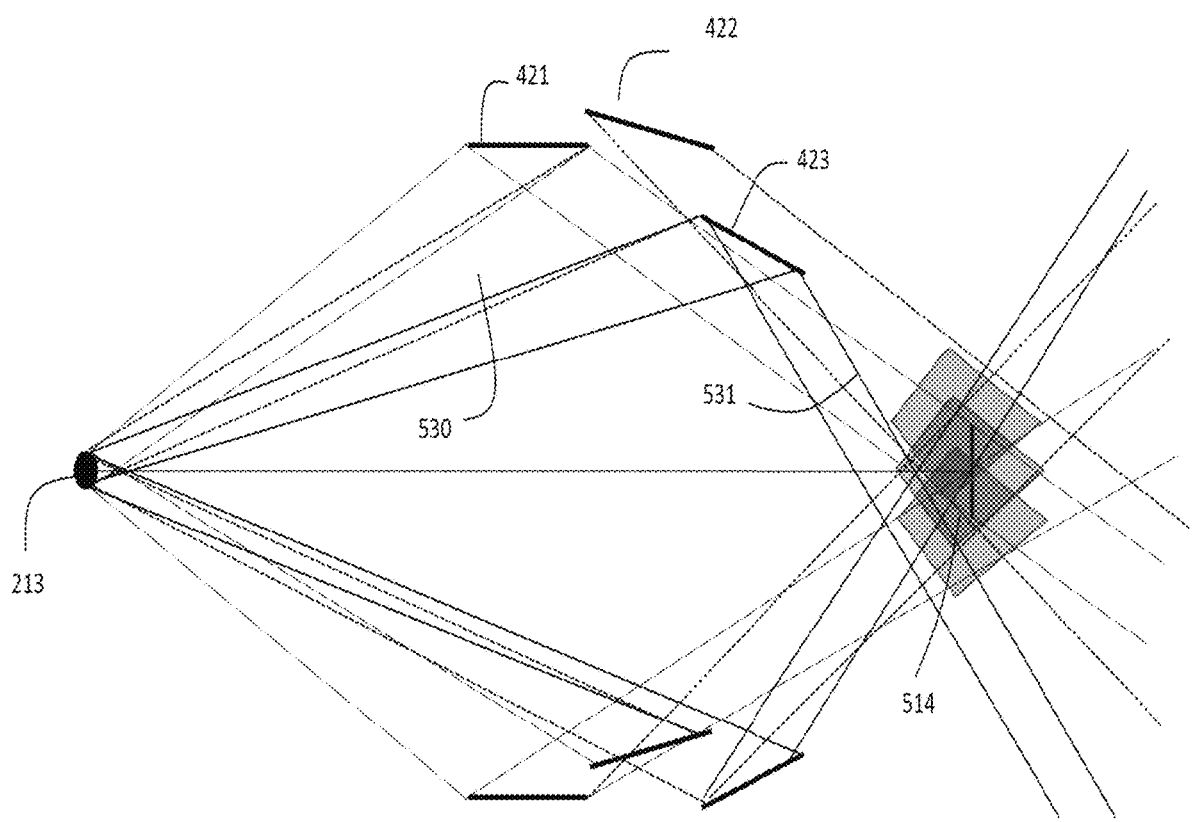

Reference is now made to FIG. 13. Showing the results of a different deviation. FIG. 13 show another example of mounting the extension rings not coaxially. Ring 421, 422 and 423 are not mounted on the same axis and might diverge in the angle of their axis. The outgoing rays (531) go to slightly different location. This assembly show that the individual images of the target deviate from one another stretching the target location to form a stretched shape (514).

These are just examples and many more deviations and techniques can be applied. One can also go to closer to theory implementation making a small treatment volume.

The main innovation of this invention is the longitudinal tiling of complete rings as tiled parts with ring extensions using planar tiles forming an extended structure, The designed possibility of deviation from the Rowland radius, the tilt angle and the off-cut angle. This can be done in more ways than the examples given.

Additional innovation is a structure that allows the adjustment of individual tiles.

All these possibilities are based on the mechanism of individual tile adjustments employing all tiles and rings.

The invention claimed is:

1. An X-ray system for providing a converging X-rays comprising:
   (a.) an X-ray source having an optical axis thereof; and
   (b.) An X-ray lens comprising at least one ring having a Bragg reflecting surface formed by a plurality of single-crystal tiles; each tile is individually comprising an adjusting arrangement enabling a tridimensional individual displacement thereof in angular and translational manner;
   wherein said adjusting arrangement comprises at least one holder adjustably secured to said at least one ring by means of three screws.

2. The X-ray system according to claim 1, wherein said Bragg reflecting surface is formed by a plurality of single-crystal tiles characterized by identical crystallographic surfaces and belonging to a number of extension rings.

3. The X-ray system according to claim 1, wherein said single-crystal tiles are processed with a non-zero offcut angle; said single-crystal tiles are spatially adjusted so that a Johansson curved surface is approximated.

4. The X-ray system according to claim 1, wherein said single-crystal tiles are processed with zero offcut angle; said single-crystal tiles are spatially adjusted so that a quasi-focusing Johann and Johannsson curvatures are approximated.

5. The X-ray system according to claim 1, wherein at least one of said three screws is spring-controlled.

6. The X-ray system according to claim 1, wherein at least one of said three screws is mounted within an eccentrically arranged bore of bushing such that rotation of said bushing provides transversal displacement of said holder secured by said at least one of said three screws.

7. The X-ray system according to claim 6, wherein said screw mounted within a diameter of said eccentrically arranged bore is sufficient for free movement therethrough in a skewed position.

* * * * *